(12) United States Patent
Shin

(10) Patent No.: US 12,330,416 B2
(45) Date of Patent: Jun. 17, 2025

(54) APPARATUS AND METHOD FOR RAPID MONITORING OF INKJET INK DROPLETS USING TIME DELAY INTEGRATION

(71) Applicant: PUKYONG NATIONAL UNIVERSITY INDUSTRY-UNIVERSITY COOPERATION FOUNDATION, Busan (KR)

(72) Inventor: Dong-Youn Shin, Busan (KR)

(73) Assignee: Pukyong National University Industry-University Cooperation Foundation, Busan (KR)

( * ) Notice: Subject to any disclaimer, the term of this patent is extended or adjusted under 35 U.S.C. 154(b) by 299 days.

(21) Appl. No.: 18/175,328

(22) Filed: Feb. 27, 2023

(65) Prior Publication Data

US 2023/0211602 A1  Jul. 6, 2023

Related U.S. Application Data

(63) Continuation of application No. PCT/KR2022/004062, filed on Mar. 23, 2022.

(30) Foreign Application Priority Data

Dec. 29, 2021  (KR) .......... 10-2021-0191479

(51) Int. Cl.
*B41J 2/045* (2006.01)
*G01N 21/85* (2006.01)
(Continued)

(52) U.S. Cl.
CPC ....... *B41J 2/04573* (2013.01); *B41J 2/04535* (2013.01); *B41J 2/0456* (2013.01);
(Continued)

(58) Field of Classification Search
None
See application file for complete search history.

(56) References Cited

U.S. PATENT DOCUMENTS 5,929,875 A * 7/1999 Su .......................... B41J 2/0458
347/19
6,400,099 B1 * 6/2002 Walker ..................... B41J 2/125
250/552
2019/0009456 A1 * 1/2019 Biskop ............. B29D 11/00951

FOREIGN PATENT DOCUMENTS

JP  2004-003930 A  1/2004
JP  2004345209 A * 12/2004  .............. B41J 2/125
(Continued)

*Primary Examiner* — Reza Aghevli
(74) *Attorney, Agent, or Firm* — Knobbe, Martens, Olson & Bear, LLP

(57) ABSTRACT

An apparatus and a method for rapid monitoring of inkjet ink droplets using time delay integration are proposed. Inkjet ink droplets used in manufacturing a display panel may be captured for a set period of time using a wide one-dimensional (1D) line scan camera to obtain a plurality of pieces of high-resolution small-amount image data. The obtained plurality of pieces of high-resolution small-amount image data may be subjected to image processing to generate ink droplet two-dimensional (2D) time-space information. The ink droplet two-dimensional (2D) time-space information may be compared with pre-stored reference ink droplet 2D time-space information to determine whether the ink droplets are normal.

17 Claims, 9 Drawing Sheets

(51) Int. Cl.
*G01N 33/32* (2006.01)
*G02F 1/1341* (2006.01)
*G06T 7/00* (2017.01)

(52) U.S. Cl.
CPC .......... *B41J 2/04561* (2013.01); *G01N 21/85* (2013.01); *G01N 33/32* (2013.01); *G02F 1/13415* (2021.01); *G06T 7/001* (2013.01); *B41J 2202/09* (2013.01); *G01N 2201/0696* (2013.01)

(56) References Cited

FOREIGN PATENT DOCUMENTS

| | | | | |
|---|---|---|---|---|
| KR | 10-2010-0110323 A | 10/2010 | | |
| KR | 10-2017-0060383 A | 6/2017 | | |
| KR | 10-2020-0141643 A | 12/2020 | | |
| WO | WO-2009076249 A2 * | 6/2009 | ............. | G01N 21/95 |
| WO | WO-2010002540 A2 * | 1/2010 | ............. | B82Y 15/00 |

* cited by examiner

APPARATUS AND METHOD FOR RAPID MONITORING OF INKJET INK DROPLETS USING TIME DELAY INTEGRATION

CROSS-REFERENCE TO RELATED APPLICATIONS

This application is a continuation application, and claims the benefit under 35 U.S.C. § 120 and § 365 of PCT Application No. PCT/KR2022/004062, filed on Mar. 23, 2022, which claims priority to Korean Patent Application No. 10-2021-0191479 filed on Dec. 29, 2021, both of which are hereby incorporated by reference in their entirety.

BACKGROUND

Technical Field

The present disclosure relates to an apparatus and a method for rapid monitoring of inkjet ink droplets using time delay integration. In particular, the present disclosure relates to an apparatus and a method for rapid monitoring of inkjet ink droplets using time delay integration, wherein inkjet ink droplets used in manufacturing a display panel are captured for a set period of time using a one-dimensional (1D) line scan camera to obtain a plurality of pieces of high-resolution small-amount image data, and the obtained plurality of pieces of high-resolution small-amount image data are subjected to image processing to generate ink droplet two-dimensional (2D) time-space information, and the ink droplet two-dimensional (2D) time-space information is compared with pre-stored reference ink droplet 2D time-space information to determine whether the ink droplets are normal.

Description of Related Technology

In a general method of constructing subpixels of a conventional display panel, a color filter of the display panel is manufactured by repeatedly performing a method of applying a color resist of one of three colors, red, green, and blue, completely on the top of the display panel and of leaving the color resist of the desired color on only the desired subpixels through a photolithography process.

SUMMARY

One aspect is an apparatus and a method for rapid monitoring of inkjet ink droplets using time delay integration, the apparatus and the method being capable of rapid monitoring, being economical with a low unit cost of manufacture, and being capable of providing high resolution.

Another aspect is an apparatus for rapid monitoring of inkjet ink droplets using time delay integration, the apparatus including: a light strobe using at least one LED or laser excited phosphor (LEP) and configured to emit light to the ink droplets dropped from an inkjet print head; a wide 1D line scan camera provided facing the light strobe and configured to capture the ink droplets with a set period to obtain high-resolution small-amount ink droplet image data; and a controller configured to collect the high-resolution small-amount ink droplet image data obtained for the set period and perform image processing on the high-resolution small-amount ink droplet image data to obtain ink droplet 2D time-space information, and compare the ink droplet 2D time-space information with pre-stored reference ink droplet 2D time-space information to determine whether the ink droplets are normal.

According to the embodiment, the apparatus for rapid monitoring of inkjet ink droplets using time delay integration may further include a display configured to display a result of determining, by the controller, whether the ink droplets are normal.

According to the embodiment, in the apparatus for rapid monitoring of inkjet ink droplets using time delay integration, when the ink droplets dropped from the inkjet print head are captured by the wide 1D line scan camera and the light strobe, a delay time $\Delta t$ for each time point at which a driving voltage is applied to the inkjet print head is calculated by following [Equation 1].

$$\Delta t = \Delta(1/f) = \text{abs}(1/f_1 - 1/f_2) \qquad \text{[Equation 1]}$$

[Herein, $1/f_1$ denotes an ink droplet discharge period of the inkjet print head, and $1/f_2$ denotes an operating period of the wide 1D line scan camera and the light strobe. Accordingly, a difference $\Delta(1/f)$ between the two periods refers to the delay time $\Delta t$ at a time point at which the 1D line scan camera and the light strobe operate each time the ink droplets are discharged]

According to the embodiment, in the apparatus for rapid monitoring of inkjet ink droplets using time delay integration, the reference ink droplet 2D time-space information may be ink droplet 2D time-space information obtained after an ink droplet volume of the inkjet print head is calibrated by equipment for ink droplet volume calibration.

According to the embodiment, in the apparatus for rapid monitoring of inkjet ink droplets using time delay integration, each of the ink droplet 2D time-space information resulting from image processing and the reference ink droplet 2D time-space information for determining whether the ink droplets are normal may be any one or more selected from a group of a start time, an end time, a maximum value, a mean value, a sum of squares of deviations, and a variance value of curves connecting ink droplet widths over time, and it may be determined that the ink droplets are in a normal state when an error between the ink droplet 2D time-space information resulting from image processing and the reference ink droplet 2D time-space information is within a set range.

According to the embodiment, in the apparatus for rapid monitoring of inkjet ink droplets using time delay integration, each of the ink droplet 2D time-space information resulting from image processing and the reference ink droplet 2D time-space information compared to determine whether the ink droplets are normal may be any one or more selected from a group of a start time, an end time, a maximum value, a minimum value, a mean value, a sum of squares of deviations, and a variance value for derivative values of curves connecting ink droplet widths over time, and it may be determined that the ink droplets are in a normal state when an error between the ink droplet 2D time-space information resulting from image processing and the reference ink droplet 2D time-space information is within a set range.

According to the embodiment, in the apparatus for rapid monitoring of inkjet ink droplets using time delay integration, the ink droplet 2D time-space information resulting from image processing and the reference ink droplet 2D time-space information compared to determine whether the ink droplets are normal may be integral values of curves connecting ink droplet widths over time, and it may be determined that the ink droplets are in a normal state when an error between the ink droplet 2D time-space information resulting from image processing and the reference ink droplet 2D time-space information is within a set range.

According to the embodiment, in the apparatus for rapid monitoring of inkjet ink droplets using time delay integration, each of the ink droplet 2D time-space information resulting from image processing and the reference ink droplet 2D time-space information compared to determine whether the ink droplets are normal may be a spatial coordinate value at a set time among spatial coordinate values for respective times, and it may be determined that the ink droplets are in a normal state when an error between the ink droplet 2D time-space information resulting from image processing and the reference ink droplet 2D time-space information is within a set range.

In order to achieve the above-described objective, according to another embodiment of the present disclosure, there is provided an apparatus for rapid monitoring of inkjet ink droplets using time delay integration, the apparatus including: a laser excited phosphor (LEP) light strobe configured to emit incoherent light, generated from a phosphor excited by a laser, to the ink droplets dropped from an inkjet print head; a wide 1D line scan camera provided facing the laser excited phosphor light strobe and configured to capture the ink droplets with a set period to obtain high-resolution small-amount ink droplet image data; and a controller configured to collect the high-resolution small-amount ink droplet image data obtained for the set period and perform image processing on the high-resolution small-amount ink droplet image data to obtain ink droplet 2D time-space information, and compare the ink droplet 2D time-space information with pre-stored reference ink droplet 2D time-space information to determine whether the ink droplets are normal.

According to the embodiment, in the apparatus for rapid monitoring of inkjet ink droplets using time delay integration, the laser excited phosphor light strobe may include: the laser configured to emit a laser beam; the phosphor configured to absorb the laser beam emitted from the laser and convert the laser beam into the incoherent light; and an optical lens configured to collimate or condense the incoherent light.

In order to achieve the above-described objective, according to still another embodiment of the present disclosure, there is provided a method for rapid monitoring of inkjet ink droplets, dropped from an inkjet print head, using time delay integration, the method including: collecting, by a controller, high-resolution small-amount ink droplet image data obtained by capturing the ink droplets, dropped from the inkjet print head, for a set period by a wide 1D line scan camera and a light strobe; performing, by the controller, image processing on the collected high-resolution small-amount ink droplet image data to generate ink droplet 2D time-space information; determining, by the controller, whether the ink droplets are normal by comparing the generated ink droplet 2D time-space information with pre-stored reference ink droplet 2D time-space information; and displaying, by the controller, a result of determining whether the ink droplets are normal, through a display (200).

According to the apparatus and the method for rapid monitoring of inkjet ink droplets using time delay integration according to the embodiments of the present disclosure, the light strobe emits light to ink droplets dropped from the inkjet print head for 1 microsecond or less, more preferably, 0.5 microseconds or less, the wide 1D line scan camera provided facing the light strobe captures the ink droplet for a set period with a variable delay time to obtain high-resolution small-amount ink droplet image data, the high-resolution small-amount ink droplet image data obtained for the set period is collected and subjected to image processing to obtain ink droplet 2D time-space information, and the ink droplet 2D time-space information is compared with pre-stored reference ink droplet 2D time-space information to determine whether the ink droplets are normal, whereby the apparatus and the method are capable of rapid monitoring, are economical with a low unit cost of manufacture, and are capable of providing high resolution.

DETAILED DESCRIPTION

Figure 1:
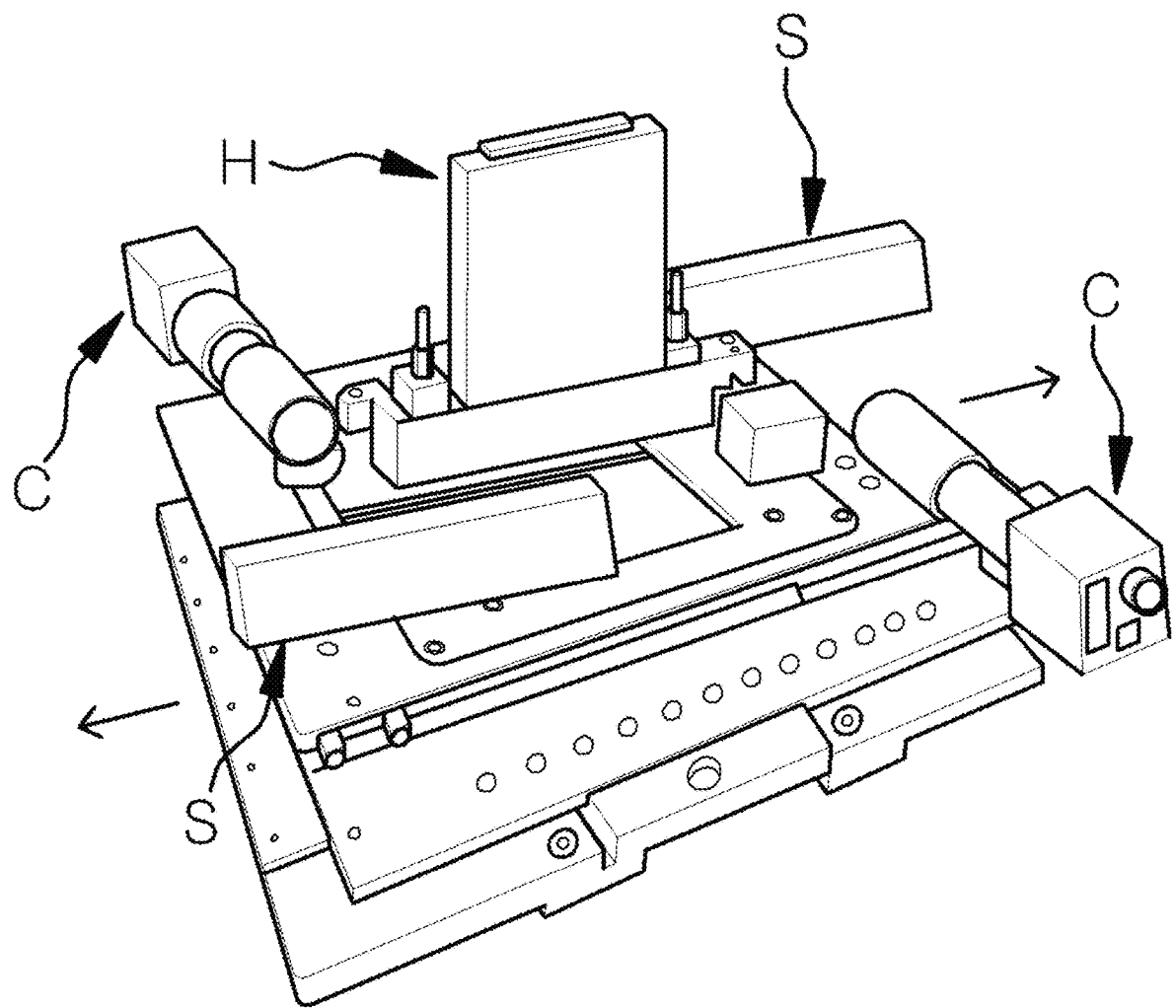
FIG. 1 is a perspective view of an apparatus for rapid monitoring of inkjet ink droplets using time delay integration according to an embodiment of the present disclosure.

In the case of this manufacturing method, waste of materials is severe and it is difficult to use the photolithography process for materials that are expensive, for example, organic light-emitting diodes (OLEDs) and quantum dots (QDs), and vulnerable to post-processing using chemicals and high temperature. Accordingly, a pattern technology, such as inkjet, capable of applying a desired amount of ink to a desired area has attracted the attention of the display industry.

In manufacturing a display panel, it is necessary to quickly inspect whether discharge of ink droplets dropped from an inkjet printer head is faulty or abnormal. In the related art, an ink droplet monitoring method using a 2D area scan camera or a laser phase Doppler measurement method is used to monitor the shape, volume, speed, discharge angle, etc. of an ink droplet from a nozzle.

However, the ink droplet monitoring method using a 2D area scan camera can observe only ink droplets discharged from several nozzles in one image frame because of a narrow Field of View (FoV), so it takes a long time to complete the inspection because tens of times of measurements or more is required in order to inspect all ink droplets discharged from hundreds to thousands of nozzles of the inkjet print head. In addition, the laser phase Doppler measurement method cannot measure the shape of an ink droplet. In particular, when an ink droplet contains particles that can scatter a laser, it is impossible to measure the volume, speed, discharge angle, etc. of the ink droplet because of scattering noise.

In describing embodiments of the present disclosure, if it is decided that a detailed description of the known art related to the present disclosure makes the subject matter of the present disclosure unclear, the detailed description will be omitted. Further, the terms described below are defined in consideration of the functions in the present disclosure, and may be changed depending on the intention of a user, an operator, or a usual practice. Therefore, the definition should be based on the contents throughout this specification. The terms used below are merely for describing the embodiments of the present disclosure, and should not be restrictively interpreted. Unless clearly used otherwise, a singular expression includes a plural meaning. In the description, the expression "include" or "have" is for indicating any features, numbers, steps, operations, elements, or a part or combination thereof, and should not be interpreted as excluding presence or possibility of one or more other features, numbers, steps, operations, elements, or a part or combination thereof other than the above.

In each system shown in the drawings, elements in some cases may have same or different reference numerals to suggest that the elements could be different or similar. However, elements may have different implementations and work with some or all of the systems shown or described in the specification. The various elements shown in the drawings may be the same or different. It is random which one is referred to as a first element and which one is referred to as a second element.

In the specification, when one element "transmits", "transfers", or "provides" data or a signal to another element, it means that the element transmits the data or signal directly to the other element or the element transmits the data or signal to the other element via at least one another element.

Hereinafter, embodiments of the present disclosure will be described in detail with reference to the accompanying drawings.

Figure 2:
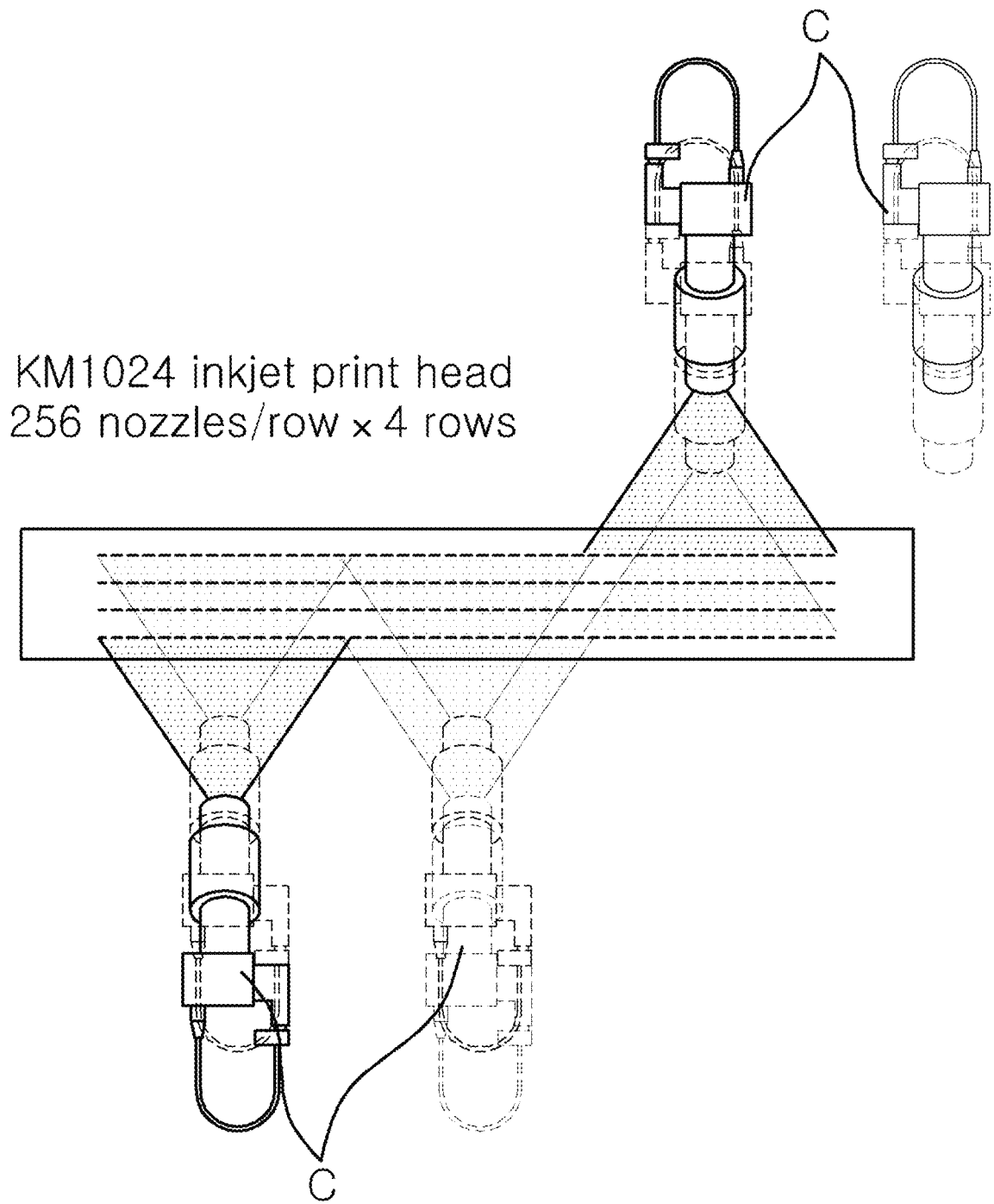
FIG. 2 is a diagram illustrating a scan path along which the wide 1D line scan camera shown in FIG. 1 moves to capture ink droplets dropped from next nozzles after capturing ink droplets from the inkjet print head.
Figure 3:
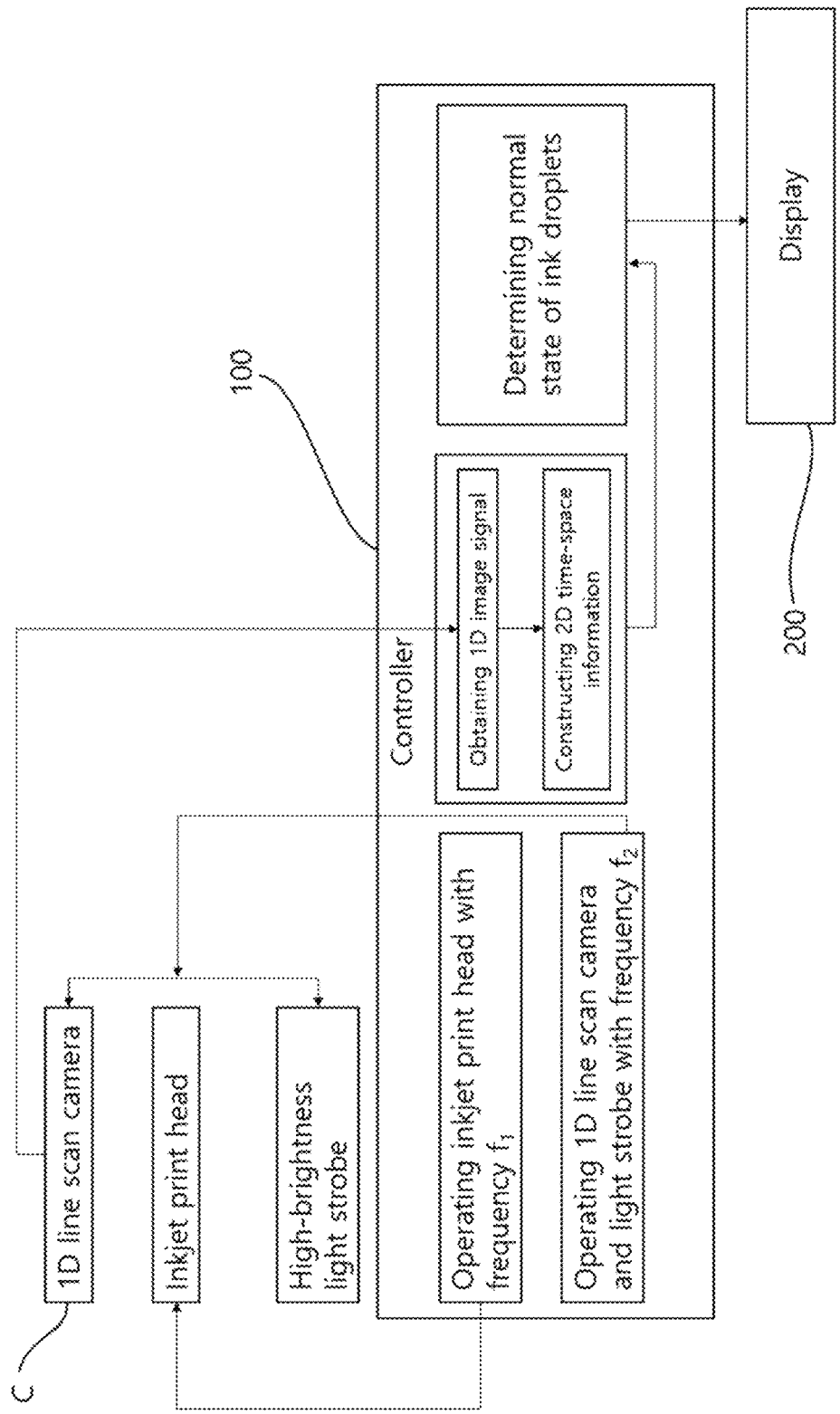
FIG. 3 is a block diagram of an apparatus for rapid monitoring of inkjet ink droplets using time delay integration according to an embodiment of the present disclosure.
Figure 5:
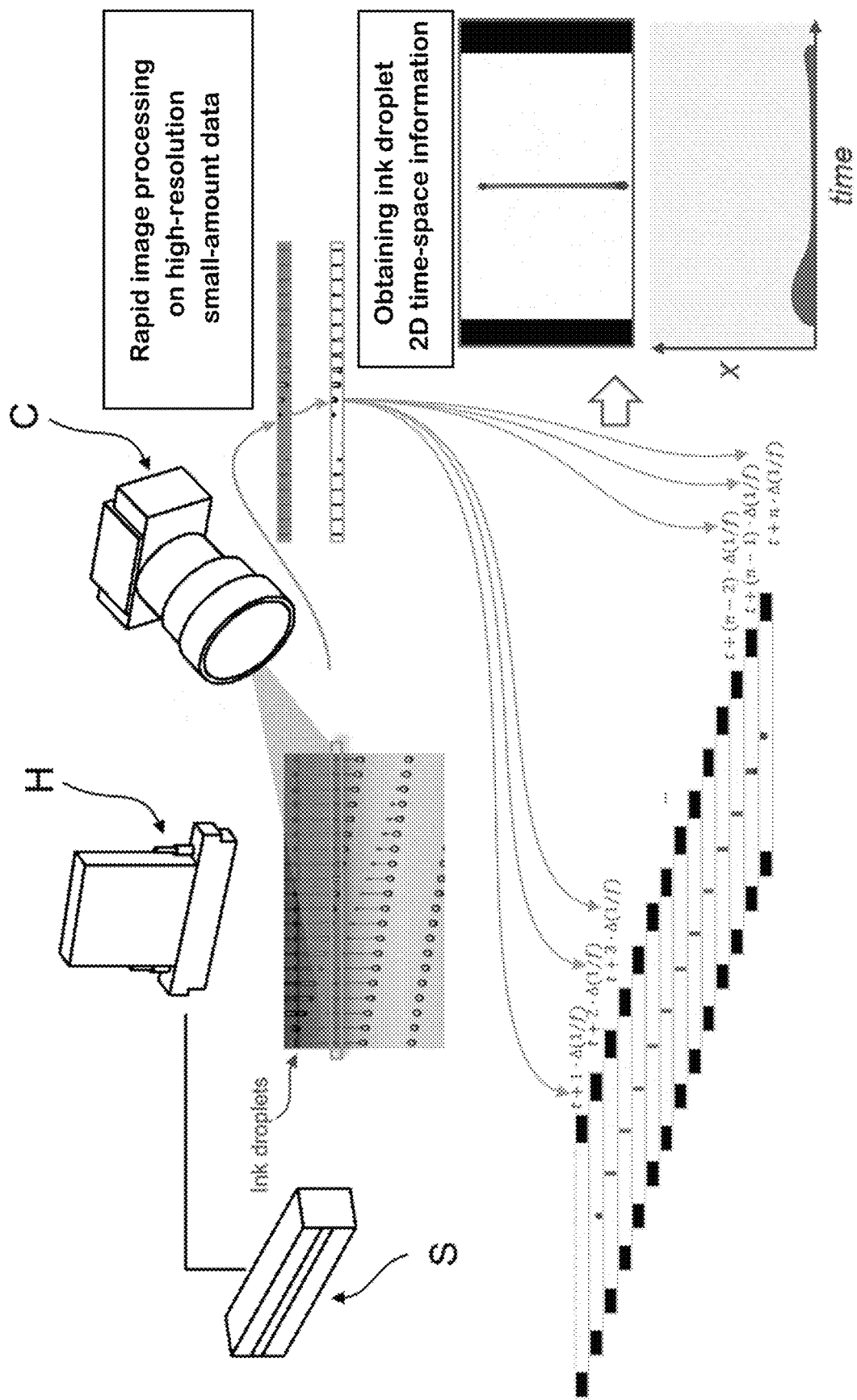
FIG. 5 is a diagram illustrating a process of obtaining ink droplet 2D time-space information by performing image processing on high-resolution small-amount ink droplet image data captured by the wide 1D line scan camera shown in FIG. 1 with a set variable delay time and for a set period.

FIG. 1 is a perspective view of an apparatus for rapid monitoring of inkjet ink droplets using time delay integration according to an embodiment of the present disclosure. FIG. 2 is a diagram illustrating a scan path along which the wide 1D line scan camera shown in FIG. 1 moves to capture next nozzles after capturing ink droplets from the inkjet print head. FIG. 3 is a block diagram of an apparatus for rapid monitoring of inkjet ink droplets using time delay integration according to an embodiment of the present disclosure. FIG. 5 is a diagram illustrating a process of obtaining ink droplet 2D time-space information by performing image processing on high-resolution small-amount ink droplet image data captured by the wide 1D line scan camera shown in FIG. 1 with a set variable delay time and for a set period.

According to an embodiment of the present disclosure, an apparatus for rapid monitoring of inkjet ink droplets using time delay integration includes a light strobe S, a wide 1D line scan camera C, a controller 100, and a display 200, as shown in FIGS. 1 and 3.

The light strobe S emits light to ink droplets dropped from an inkjet print head H. For example, as shown in FIG. 1, the light strobe S and the wide 1D line scan camera C in a pair are provided in front of and behind the inkjet print head H, respectively, to capture 1D images of ink droplets dropped from the inkjet print head H.

The light strobe S may be in the form of a cluster or bar including at least one high-brightness LED. Alternatively, the light strobe S may be a high-brightness sub-microsecond pulse light strobe that uses a laser excited phosphor (LEP) method, in which incoherent light is obtained by emitting a laser of a short wavelength to a phosphor plate, and is thus capable of operating with a short pulse of 1 microsecond or less, more preferably, an ultra-short pulse of 0.5 microseconds or less.

The wide 1D line scan camera C is provided facing the light strobe S and captures ink droplets with a set period to obtain 1D high-resolution small-amount ink droplet image data. For example, as shown in FIGS. 1 and 2, assuming that in the inkjet print head H, four rows of 256 nozzles are arranged, that is, a total of 1024 nozzles are provided, the wide 1D line scan camera C and the light strobe S, which are respectively installed in front of and behind the inkjet print head H, are configured to capture images of ink droplets discharged from a plurality of nozzles in a row. In particular, a case of providing wide 1D line scan cameras Cs and light strobes Ss in two pairs facing each other in a lateral direction enables twice as many nozzles to be observed as a case of providing a wide 1D line scan camera C and a light strobe S in a pair only, so that all nozzles of the inkjet print head can be monitored rapidly and within a short time.

Assuming that a discharge frequency of ink droplets discharged from the inkjet print head is $f_1$, an operating frequency of the wide 1D line scan camera C and the light strobe S is equal to $f_1$ and a delay time is variable with respect to a start point of a driving voltage applied to the inkjet print head H, so that sequential pieces of 1D high-resolution small-amount image data over time are obtained. Herein, the controller 100 needs to intervene so that the wide 1D line scan camera C and the light strobe S operate at a time point more delayed by Δt than previously each time image capturing is performed. That is, the controller 100 receives a capturing end signal of the wide 1D line scan camera C and the light strobe S, and adds Δt to the previous delay time accordingly to set a new delay time for next capturing, and transmits a signal informing the wide 1D line scan camera C and the light strobe S of a new operating time point according to the varied delay time.

Figure 4:
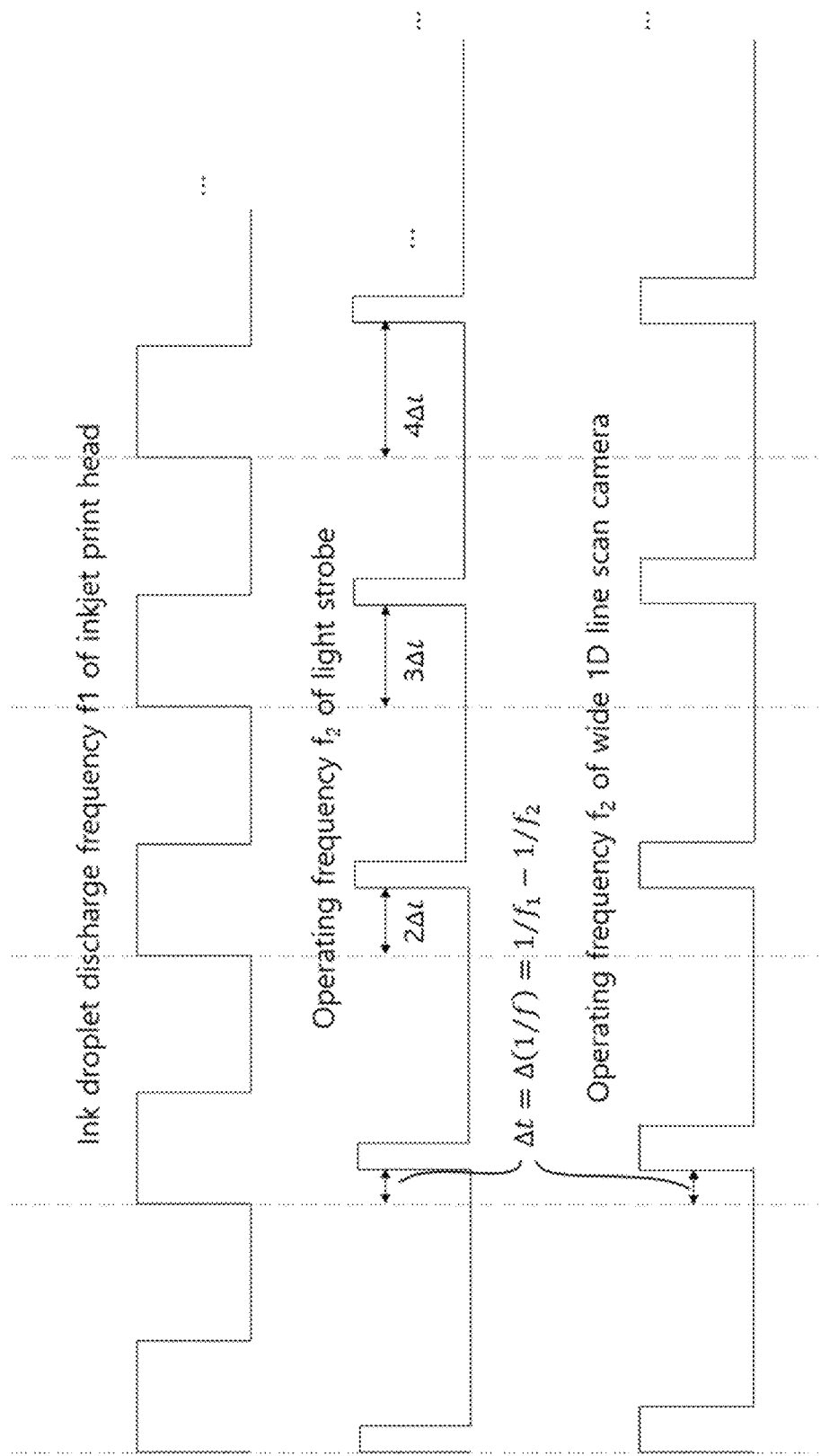
FIG. 4 is an exemplary diagram illustrating that an ink droplet discharge frequency $f_1$ of an inkjet print head and an operating frequency $f_2$ of a wide 1D line scan camera C and a light strobe S are set different, so that a delay time for each driving period of the inkjet print head is automatically variable without interference from a controller.

In order to avoid the complexity of controlling the wide 1D line scan camera C and the light strobe S for ink droplet capturing, the ink droplet discharge frequency $f_1$ of the inkjet print head H and the operating frequency $f_2$ of the wide 1D line scan camera C and the light strobe S may be set different. As shown in FIG. 4, when the operating frequency $f_1$ of the inkjet print head and the operating frequency $f_2$ of the wide 1D line scan camera and the light strobe are set different, the delay time Δt for each driving period of the inkjet print head may be calculated by [Equation 1] below, and a variable delay time is the total sum of Δt for which delay takes place for each driving period.

$$\Delta t = \Delta(1/f) = \text{abs}(1/f_1 - 1/f_2) \quad \text{[Equation 1]}$$

[Herein, $f_1$ denotes the operating frequency of the inkjet print head, and $f_2$ denotes the operating frequency of the wide 1D line scan camera and the light strobe. Accordingly, $1/f_1$ denotes an ink droplet discharge period of the inkjet print head, $1/f_2$ denotes an operating period of the wide 1D line scan camera and the light strobe, and a difference $\Delta(1/f)$ between the two periods refers to the delay time $\Delta t$ at a time point at which the 1D line scan camera and the light strobe operate each time the ink droplets are discharged].

As described above, when the discharge frequency $f_1$ of the inkjet print head H and the operating frequency $f_2$ of the wide 1D line scan camera C and the LED strobe S are set different, the controller 100 does not have to interfere to change a delay time every capturing, so it is convenient to perform control. In addition, since the wide 1D line scan camera C performs capturing with a period of the difference $\Delta(1/f)$ between the reciprocals of the two frequencies, high time resolution may be provided.

Referring to FIG. 3, the controller 100 is a microcomputer that controls all elements in the present disclosure, and is configured to: operate the inkjet print head H, the wide 1D line scan camera C, and the light strobe S; collect pieces of 1D high-resolution small-amount ink droplet image data obtained for a set period by the wide 1D line scan camera C; perform image processing on the collected pieces of the 1D high-resolution small-amount ink droplet image data to obtain ink droplet 2D time-space information; compare the obtained ink droplet 2D time-space information with pre-stored reference ink droplet 2D time-space information to determine whether the ink droplets are normal; and output a display control signal corresponding determination to the display 200.

The reference ink droplet 2D time-space information is ink droplet 2D time-space information that is obtained after the ink droplet volume of the inkjet print head H is calibrated by equipment for ink droplet volume calibration.

Assuming that only one of the plurality of nozzles of the inkjet print head H discharges ink droplets for convenience of description, FIG. 5 illustrates a process in which the controller 100 collects pieces of 1D high-resolution small-amount ink droplet image data obtained by the wide 1D line scan camera C for a set period and performs image processing on the pieces of 1D high-resolution small-amount ink droplet image data to obtain ink droplet 2D time-space information.

Figure 6A:
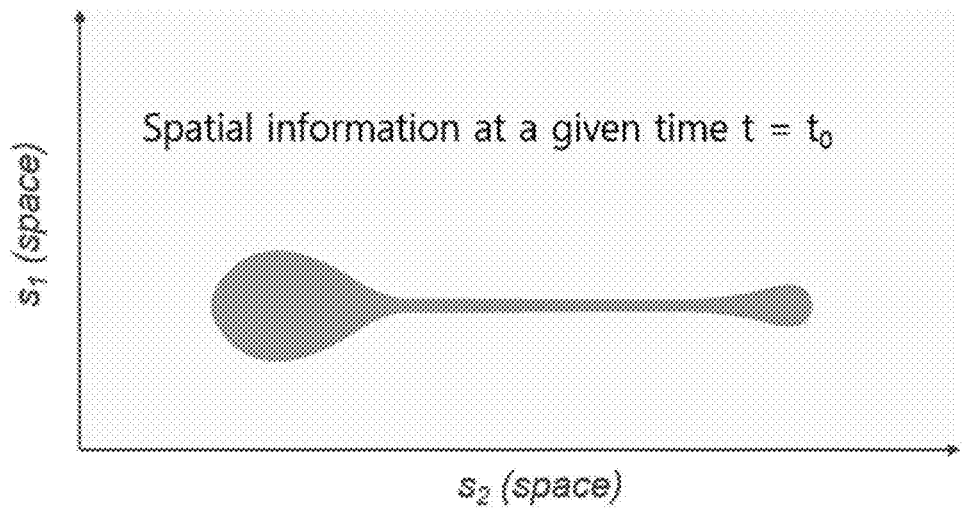
FIG. 6A shows that space-space image information is obtained when ink droplets are captured at a particular time using a conventional 2D area camera
Figure 6B:
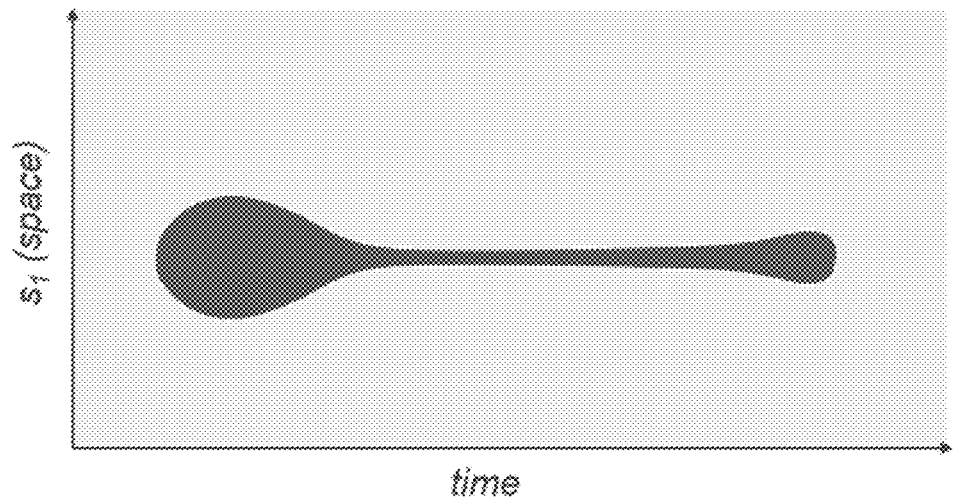
FIG. 6B shows an image obtained by visualizing 2D time-space information by reconstructing 1D space information of ink droplets captured at different times with a 1D line scan camera through integration over time according to the present disclosure.

FIG. 6A shows that 2D space-space image information is obtained when ink droplets are captured at a particular time using a conventional 2D area camera. Conversely, FIG. 6B shows a 2D time-space image obtained by capturing lateral-direction 1D space images of ink droplets with respective delay times accumulated by $\Delta t$ for each capturing, and by stacking up the 1D space images over time when the 1D line scan camera is used as in the present disclosure.

The time-space graph shown at the lower right of FIG. 5 refers to ink droplet 2D time-space information resulting from image processing, and is compared with stored reference ink droplet 2D time-space information so that whether the ink droplets are normal may be determined.

A process of determining whether ink droplets are normal will be described in detail.

Figure 7:
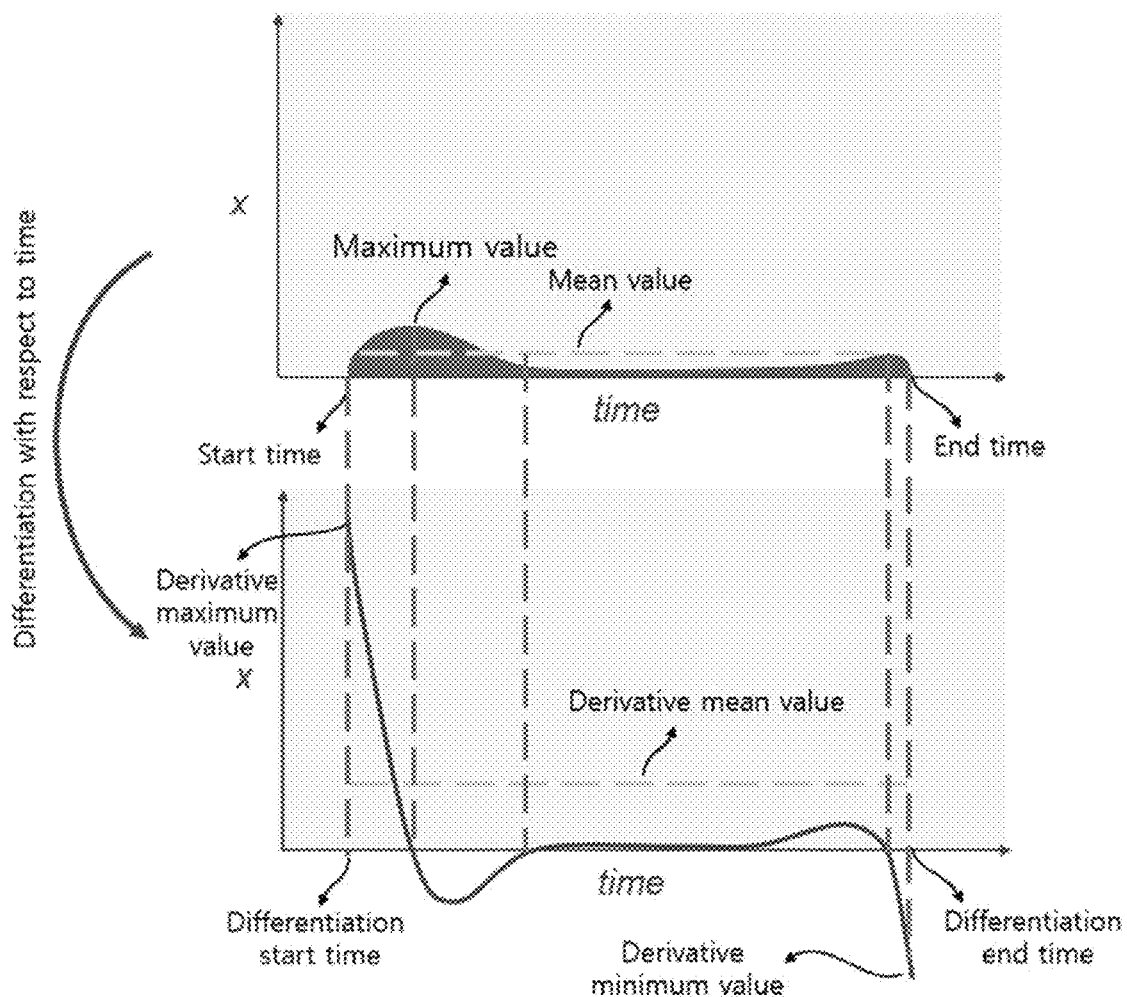
FIG. 7 is an exemplary diagram illustrating ink droplet 2D time-space information resulting from image processing and a result of mathematical differentiation thereof.

First, assuming that each of the ink droplet 2D time-space information resulting from image processing and the reference ink droplet 2D time-space information is defined as any one or more selected from the group of a start time at which the ink droplets are measured, an end time, a maximum value, a mean value, a sum of the squares of deviations of the two pieces of the 2D time-space information, and a variance value thereof as shown in the upper graph of FIG. 7, it is determined that the ink droplets are in a normal state when errors between the ink droplet 2D time-space information resulting from image processing and the reference ink droplet 2D time-space information are in a set range, or it is determined that the ink droplets are in an abnormal state when at least one of the errors is out of the set range.

Second, assuming that each of the ink droplet 2D time-space information resulting from image processing and the reference ink droplet 2D time-space information is defined as any one or more selected from the group of a start time, an end time, a maximum value, a minimum value, a mean value for derivative values of curves connecting ink droplet widths over time, a sum of the squares of deviations of two 2D time-space derivative curves, and a variance value thereof as shown in the lower graph of FIG. 7, it is determined that the ink droplets are in a normal state when errors between the ink droplet 2D time-space information resulting from image processing and the reference ink droplet 2D time-space information are in a set range, or it is determined that the ink droplets are in an abnormal state when at least one of the errors is out of the set range.

Third, assuming that both the ink droplet 2D time-space information resulting from image processing and the reference ink droplet 2D time-space information are defined as integral values of curves connecting ink droplet widths over time, an error between the ink droplet 2D time-space information resulting from image processing and the reference ink droplet 2D time-space information is obtained, and it is determined that the ink droplets are in a normal state when the error is in a set range, or it is determined that the ink droplets are in an abnormal state when the error is out of the set range.

Fourth, assuming that each of the ink droplet 2D time-space information resulting from image processing and the reference ink droplet 2D time-space information is defined as a spatial coordinate value at a particular time (set time) among spatial coordinate values for respective times, an error between the ink droplet 2D time-space information resulting from image processing and the reference ink droplet 2D time-space information is obtained, and it is determined that the ink droplets are in a normal state when the error is in a set range, or it is determined that the ink droplets in an abnormal state when the error is out of the set range.

The display 200 displays a result of determining, by the controller 100, whether the ink droplets are normal. Displayed items may include whether the ink droplet are normal as well as a 1D high-resolution small-amount ink droplet image obtained by the 1D line scan camera C and ink droplet 2D time-space information generated by performing image processing.

Described will be a method for rapid monitoring of ink droplets using an apparatus, configured as described above, for rapid monitoring of inkjet ink droplets using time delay integration according to an embodiment of the present disclosure.

Figure 8:
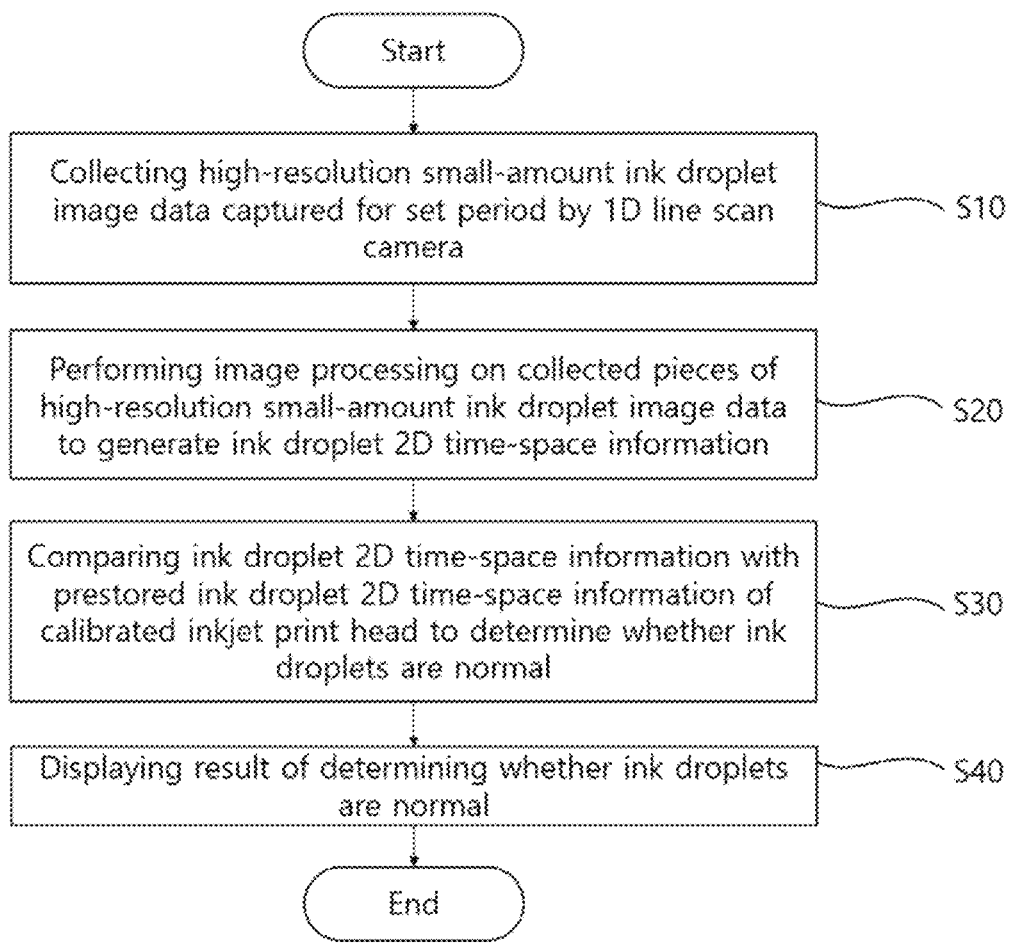
FIG. 8 is a flowchart illustrating a method for rapid monitoring of inkjet ink droplets using time delay integration according to an embodiment of the present disclosure.

FIG. 8 is a flowchart illustrating a method for rapid monitoring of inkjet ink droplets using time delay integration according to an embodiment of the present disclosure. Herein, S denotes a step.

Before describing the method for rapid monitoring of inkjet ink droplets, it is assumed that at least one LED strobe S has emitted light the ink droplets dropped from the inkjet print head H and the wide 1D line scan camera C has captured the ink droplets for a set period and 1D high-resolution small-amount ink droplet image data has been obtained thus.

First, the controller 100 collects the 1D high-resolution small-amount ink droplets image data in step S10, which has been obtained by capturing the ink droplets for the set period by the wide 1D line scan camera C and the LED strobe S.

Next, the controller 100 performs image processing on the 1D high-resolution small-amount ink droplet image data collected in step S10 to generate ink droplet 2D time-space information in step S20.

Next, the controller 100 compares the ink droplet 2D time-space information generated in step S20 with pre-stored reference ink droplet 2D time-space information (information of the inkjet printer head calibrated) to determine whether the ink droplets are normal in step S30.

Next, the controller 100 displays a result of determining whether the ink droplets are normal, through the display 200 in step S40.

Although the use of at least one LED strobe to emit light to ink droplets dropped from the inkjet print head has been described as an example, a laser excited phosphor (LEP) strobe may be employed instead of the LED strobe. The LEP strobe using LEP utilizes a laser beam and a phosphor for the ink droplets dropped from the inkjet print head.

Figure 9:
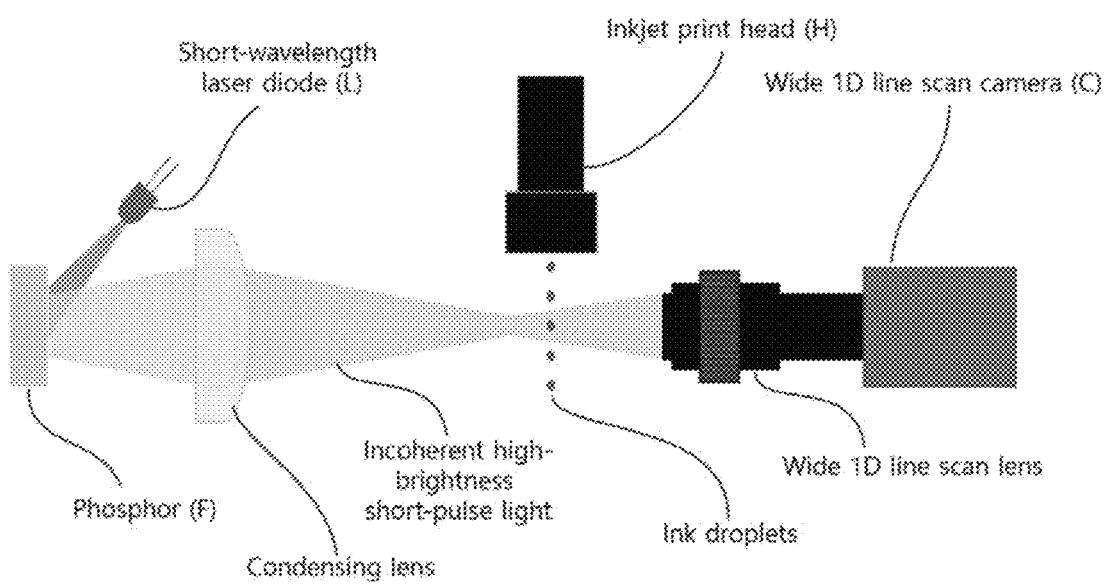
FIG. 9 is a diagram illustrating a configuration of a laser excited phosphor light strobe, which uses a laser and a phosphor, and a wide 1D line scan camera of an apparatus for rapid monitoring of inkjet ink droplets using time delay integration according to an embodiment of the present disclosure.

As shown in FIG. 9, a phosphor (F) that generates incoherent light by absorbing a laser beam emitted from a laser L is included, and dropping ink droplets are irradiated with the incoherent light emitted from the phosphor. A collimating or condensing lens may be further included. By emitting a laser to the phosphor as described above, the laser excited phosphor (LEP) strobe for generating incoherent light enables high-brightness illumination with an ultra-short pulse of 1 microsecond or less, particularly, 0.5 microseconds or less, compared to a strobe using a general LED, so that an ink droplet image of ultra-high quality can be obtained.

According to an apparatus and a method for rapid monitoring of inkjet ink droplets using time delay integration according to the embodiments of the present disclosure, an LED or LEP light strobe emits light to ink droplets dropped from the inkjet print head, a wide 1D line scan camera is provided facing the light strobe and captures the ink droplets with a set period to obtain high-resolution small-amount ink droplet image data, the high-resolution small-amount ink droplet image data obtained for the set period is collected and subjected to image processing to obtain ink droplet 2D time-space information, and the ink droplet 2D time-space information is compared with pre-stored reference ink droplet 2D time-space information to determine whether the ink droplets are normal, whereby the apparatus and the method are capable of rapid monitoring, are economical with a low unit cost of manufacture, and are capable of providing high resolution. In addition, unlike 2D space-space information that a camera of a conventional 2D area scan type provides, 2D time-space information with high time resolution is provided, so that whether ink droplets are normal can be determined with high sensitivity.

The optimum exemplary embodiments have been disclosed and the specific terms are used in the drawings and the specification, but the exemplary embodiments and the terms are used just for the purpose of describing the exemplary embodiments of the present disclosure, but not used to limit meanings or restrict the scope of the present disclosure disclosed in the claims. Therefore, those skilled in the art will understand that various modifications of the exemplary embodiment and any other exemplary embodiments equivalent thereto are available. Accordingly, the true technical protection scope of the present disclosure should be determined by the technical idea of the appended claims.

What is claimed is:

1. An apparatus for rapid monitoring of inkjet ink droplets using time delay integration, the apparatus comprising:
   a light strobe using at least one light emitting diode (LED) or laser excited phosphor and configured to emit light to the ink droplets dropped from an inkjet print head;
   a wide 1D line scan camera provided facing the light strobe and configured to capture the ink droplets with a set period to obtain high-resolution small-amount ink droplet image data; and
   a controller configured to:
   collect the high-resolution small-amount ink droplet image data obtained for the set period and perform image processing on the high-resolution small-amount ink droplet image data to obtain ink droplet 2D time-space information, and
   compare the ink droplet 2D time-space information with pre-stored reference ink droplet 2D time-space information to determine whether the ink droplets are normal.

2. The apparatus of claim 1, further comprising
   a display configured to display a result of determining, by the controller, whether the ink droplets are normal.

3. The apparatus of claim 1, wherein when the ink droplets dropped from the inkjet print head are captured by the wide 1D line scan camera and the light strobe, a delay time for each time point at which a driving voltage is applied to the inkjet print head is calculated by following [Equation 1], $$\Delta t = \Delta(1/f) = \mathrm{abs}(1/f_1 - 1/f_2) \qquad \text{[Equation 1]}$$

[Herein, $1/f_1$ denotes an ink droplet discharge period of the inkjet print head, and $1/f_2$ denotes an operating period of the wide 1D line scan camera and the light strobe; accordingly, a difference $\Delta(1/f)$ between the two periods refers to the delay time $\Delta t$ at a time point at which the 1D line scan camera and the light strobe operate each time the ink droplets are discharged].

4. The apparatus of claim 1, wherein the reference ink droplet 2D time-space information comprises ink droplet 2D time-space information obtained after an ink droplet volume of the inkjet print head is calibrated by equipment for ink droplet volume calibration.

5. The apparatus of claim 1, wherein each of the ink droplet 2D time-space information resulting from image processing and the reference ink droplet 2D time-space information for determining whether the ink droplets are normal comprises one or more of a start time, an end time, a maximum value, a mean value, a sum of squares of deviations, or a variance value of curves connecting ink droplet widths over time, and
   wherein the controller is configured to determine that the ink droplets are in a normal state in response to an error between the ink droplet 2D time-space information resulting from image processing and the reference ink droplet 2D time-space information being within a set range.

6. The apparatus of claim 1, wherein each of the ink droplet 2D time-space information resulting from image processing and the reference ink droplet 2D time-space information compared to determine whether the ink droplets are normal comprises one or more of a start time, an end time, a maximum value, a minimum value, a mean value, a sum of squares of deviations, or a variance value for derivative values of curves connecting ink droplet widths over time, and wherein the controller is configured to determine that the ink droplets are in a normal state in response to an error between the ink droplet 2D time-space information resulting from image processing and the reference ink droplet 2D time-space information being within a set range.

7. The apparatus of claim 1, wherein the ink droplet 2D time-space information resulting from image processing and the reference ink droplet 2D time-space information compared to determine whether the ink droplets are normal comprises integral values of curves connecting ink droplet widths over time, and wherein the controller is configured to determine that the ink droplets are in a normal state in response to an error between the ink droplet 2D time-space information resulting from image processing and the reference ink droplet 2D time-space information being within a set range.

8. The apparatus of claim 1, wherein each of the ink droplet 2D time-space information resulting from image processing and the reference ink droplet 2D time-space information compared to determine whether the ink droplets are normal comprises a spatial coordinate value at a set time among spatial coordinate values for respective times, and wherein the controller is configured to determine that the ink droplets are in a normal state in response to an error between the ink droplet 2D time-space information resulting from image processing and the reference ink droplet 2D time-space information being within a set range.

9. An apparatus for rapid monitoring of inkjet ink droplets using time delay integration, the apparatus comprising:
a laser excited phosphor light strobe configured to emit incoherent light, generated from a phosphor excited by a laser, to the ink droplets dropped from an inkjet print head;
a wide 1D line scan camera provided facing the laser excited phosphor light strobe and configured to capture the ink droplets with a set period to obtain high-resolution small-amount ink droplet image data; and
a controller configured to:
collect the high-resolution small-amount ink droplet image data obtained for the set period and perform image processing on the high-resolution small-amount ink droplet image data to obtain ink droplet 2D time-space information, and
compare the ink droplet 2D time-space information with pre-stored reference ink droplet 2D time-space information to determine whether the ink droplets are normal.

10. The apparatus of claim 9, wherein the laser excited phosphor light strobe comprises:
the laser configured to emit a laser beam;
the phosphor configured to absorb the laser beam emitted from the laser and convert the laser beam into the incoherent light; and
an optical lens configured to collimate or condense the incoherent light.

11. A method for rapid monitoring of inkjet ink droplets, dropped from an inkjet print head, using time delay integration, the method comprising:
collecting, by a controller, high-resolution small-amount ink droplet image data obtained by capturing the ink droplets, dropped from the inkjet print head, for a set period by a wide 1D line scan camera and a light strobe;
performing, by the controller, image processing on the collected high-resolution small-amount ink droplet image data to generate ink droplet 2D time-space information;
determining, by the controller, whether the ink droplets are normal by comparing the generated ink droplet 2D time-space information with pre-stored reference ink droplet 2D time-space information; and
displaying, by the controller, a result of determining whether the ink droplets are normal, through a display.

12. The method of claim 11, wherein when the ink droplets dropped from the inkjet print head are captured by the wide 1D line scan camera and the light strobe, a delay time for each time point at which a driving voltage is applied to the inkjet print head is calculated by following [Equation 1], $$\Delta t = \Delta(1/f) = \mathrm{abs}(1/f_1 - 1/f_2) \qquad \text{[Equation 1]}$$

[Herein, $1/f_1$ denotes an ink droplet discharge period of the inkjet print head, and $1/f_2$ denotes an operating period of the wide 1D line scan camera and the light strobe; accordingly, a difference $\Delta(1/f)$ between the two periods refers to the delay time $\Delta t$ at a time point at which the 1D line scan camera and the light strobe operate each time the ink droplets are discharged].

13. The method of claim 11, wherein the reference ink droplet 2D time-space information comprises ink droplet 2D time-space information obtained after an ink droplet volume of the inkjet print head is calibrated by equipment for ink droplet volume calibration.

14. The method of claim 11, wherein in determining whether the ink droplets are normal, each of the ink droplet 2D time-space information resulting from image processing and the reference ink droplet 2D time-space information compared to determine whether the ink droplets are normal comprises one or more of a start time, an end time, a maximum value, a mean value, a sum of squares of deviations, or a variance value of curves connecting ink droplet widths over time, and wherein the controller determines that the ink droplets are in a normal state in response to an error between the ink droplet 2D time-space information resulting from image processing and the reference ink droplet 2D time-space information being within a set range.

15. The method of claim 11, wherein in determining whether the ink droplets are normal, each of the ink droplet 2D time-space information resulting from image processing and the reference ink droplet 2D time-space information compared to determine whether the ink droplets are normal comprises one or more of a start time, an end time, a maximum value, a minimum value, a mean value, a sum of squares of deviations, or a variance value for derivative values of curves connecting ink droplet widths over time, and wherein the controller determines that the ink droplets are in a normal state in response to an error between the ink droplet 2D time-space information resulting from image processing and the reference ink droplet 2D time-space information being within a set range.

16. The method of claim 11, wherein in determining whether the ink droplets are normal, the ink droplet 2D time-space information resulting from image processing and the reference ink droplet 2D time-space information compared to determine whether the ink droplets are normal comprises integral values of curves connecting ink droplet widths over time, and wherein the controller determines that the ink droplets are in a normal state in response to an error between the ink droplet 2D time-space information resulting from image processing and the reference ink droplet 2D time-space information being within a set range.

17. The method of claim 11, wherein in determining whether the ink droplets are normal, each of the ink droplet 2D time-space information resulting from image processing and the reference ink droplet 2D time-space information compared to determine whether the ink droplets are normal comprises a spatial coordinate value at a set time among spatial coordinate values for respective times, and wherein the controller determines that the ink droplets are in a normal state in response to an error between the ink droplet 2D time-space information resulting from image processing and the reference ink droplet 2D time-space information being within a set range.

* * * * *